United States Patent
Benaron et al.

[11] Patent Number: 5,987,346
[45] Date of Patent: Nov. 16, 1999

[54] DEVICE AND METHOD FOR CLASSIFICATION OF TISSUE

[76] Inventors: David A. Benaron, 4370 Alpine Rd. #203, Portola Valley, Calif. 94028; Boris Rubinsky, 1619 Sonoma Ave., Albany, Calif. 94707

[21] Appl. No.: 08/771,952

[22] Filed: Dec. 23, 1996

Related U.S. Application Data

[63] Continuation-in-part of application No. 08/024,278, Feb. 26, 1993, Pat. No. 5,746,210.

[51] Int. Cl.$^6$ ........................................................ A61B 6/00
[52] U.S. Cl. ........................... 600/407; 600/475; 600/477
[58] Field of Search ..................................... 600/473–478, 600/310, 567; 606/2, 14, 15, 16, 167, 172, 173, 170, 207, 205, 211, 139, 140; 607/88, 89; 356/432, 433, 435; 433/29, 31

[56] References Cited

U.S. PATENT DOCUMENTS

| | | | |
|---|---|---|---|
| 3,638,640 | 2/1972 | Shaw | 128/2 R |
| 3,674,008 | 7/1972 | Johnson | 128/2 A |
| 4,555,179 | 11/1985 | Langerholc et al. | 356/342 |
| 4,718,417 | 1/1988 | Kittrell et al. | 600/476 |
| 4,773,097 | 9/1988 | Suzaki et al. | 382/6 |
| 4,805,623 | 2/1989 | Jobels | 128/633 |
| 4,810,875 | 3/1989 | Wyatt | 250/227 |
| 4,910,404 | 3/1990 | Cho et al. | 250/358.1 |
| 4,948,974 | 8/1990 | Nelson et al. | 250/358.1 |
| 4,972,331 | 11/1990 | Chance | 364/550 |
| 4,975,581 | 12/1990 | Robinson et al. | 250/339 |
| 5,070,874 | 12/1991 | Barnes et al. | 128/633 |
| 5,088,493 | 2/1992 | Giannini et al. | 128/633 |
| 5,099,123 | 3/1992 | Harjunmaa | 250/345 |
| 5,119,815 | 6/1992 | Chance | 128/633 |
| 5,137,355 | 8/1992 | Barbour et al. | 356/342 |
| 5,148,022 | 9/1992 | Kawaguchi et al. | 250/341 |
| 5,203,339 | 4/1993 | Knuttel et al. | 128/665 |
| 5,213,105 | 5/1993 | Gratton et al. | 128/664 |
| 5,257,087 | 10/1993 | Furaya | 356/336 |
| 5,275,168 | 1/1994 | Reintjes et al. | 128/665 |
| 5,280,788 | 1/1994 | Janes et al. | 128/665 |
| 5,303,026 | 4/1994 | Strobl et al. | 600/476 |
| 5,333,610 | 8/1994 | Hirao | 128/633 |
| 5,348,018 | 9/1994 | Alfano et al. | 128/665 |
| 5,371,368 | 12/1994 | Alfano et al. | 250/341.1 |
| 5,385,143 | 1/1995 | Aoyagi | 128/633 |
| 5,447,159 | 9/1995 | Schultz | 128/665 |
| 5,596,992 | 1/1997 | Haaland et al. | 128/664 |
| 5,792,053 | 8/1998 | Skladnev et al. | 600/407 |
| 5,800,350 | 9/1998 | Coppleson et al. | 600/372 |

*Primary Examiner*—Brian L. Casler
*Attorney, Agent, or Firm*—Flehr Hohbach Test Albritton & Herbert LLP

[57] ABSTRACT

A diagnostic monitor for classifying biological tissue in which a light emitter (102) is optically coupled to the tissue to be diagnosed (145) and a light detector (174) is optically coupled to the tissue to detect a portion of the light which passes through the tissue. The tissue classifier (184) receives a signal from the detector and provides an optical classification output signal (195), wherein the tissue is classified by type or state, either for detection, localization, or imaging. A method of classifying tissue is also described.

66 Claims, 14 Drawing Sheets

(4 of 14 Drawing Sheet(s) Filed in Color)

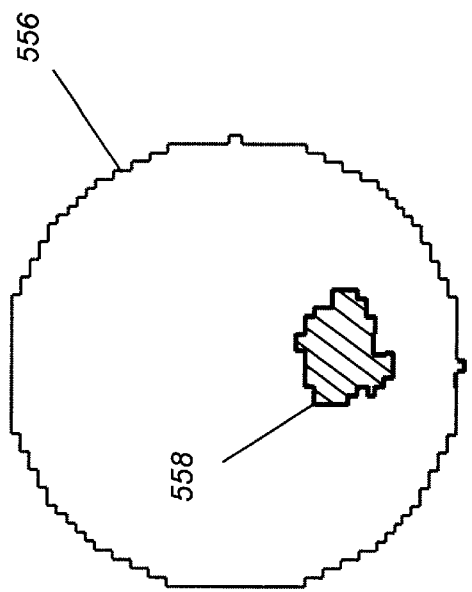
Fig. 10B
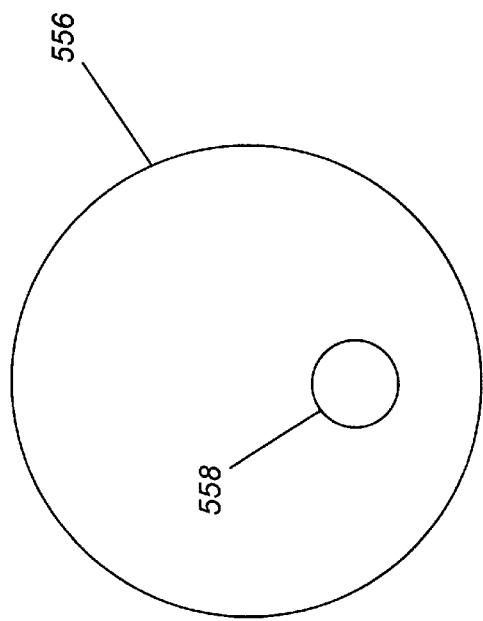
Fig. 10A
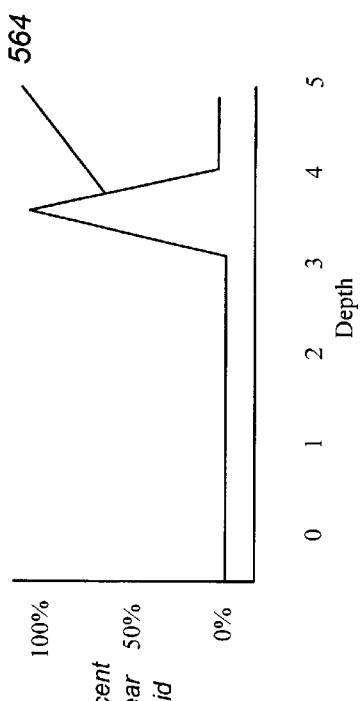
Fig. 10D
Fig. 10C

DEVICE AND METHOD FOR CLASSIFICATION OF TISSUE

RELATED APPLICATIONS

This application is a continuation-in-part of U.S. Ser. No. 08/024,278, filed Feb. 26, 1993, now U.S. Pat. No. 5,746,210 incorporated herein in its entirety by reference. In addition, the related U.S. applications of Benaron et al., Ser. Nos. 07/499,084 filed Mar. 26, 1990 (now abandoned), 07/612,808 filed Nov. 13, 1990 (now abandoned), and any continuations, continuations-in-part, or divisions are incorporated in their entirety by reference.

FIELD OF THE INVENTION

The present invention relates to a device and method for detecting, localizing, and imaging in a radiation-scattering medium, and more particularly relates to an optical device and method for measuring information regarding the interaction of emitted light with biological tissue during passage of light through the tissue, and using said information to classify the tissue by type or state, either for detection, localization, or imaging.

BACKGROUND OF THE INVENTION

A major portion of time spent in medicine is directed toward the problem of diagnosis, and a large proportion of the errors in medicine are made here. A delayed diagnosis raises the level of pain and suffering, and may allow progression to the point of irreversibility; an incorrect diagnosis can be even worse, leading to treatment that is at best unnecessary and at worst harmful or fatal.

Medical imaging, while highly sophisticated, usually merely images body structure without classification into tissue type. For example, an X-ray shows light and dark areas, but it is up to the physician to decide what is "bone" and what is "tissue." Thus, the classification of tissue by type is left to a human decision, or to a posteriori classification rules. A more accurate tissue-type diagnosis usually requires surgical tissue removal (such as biopsy) and subsequent analysis by a pathologist, but still this decision is based upon subjective classification by eye, touch, chemical analysis, or even upon the absorption of exogenous dyes. Currently, it is quite easy to misdiagnose many lesions, as widely different tissues (such as nerves or lymph ducts) may look similar upon first glance.

Light penetrates tissue in small amounts, particularly in wavelengths between 200 nm and 100 $\mu$m, with the best deep penetration achieved at wavelengths between 600 nm and 1200 nm. The light that does pass through tissue emerges bearing a signature of the tissue through which it passed, and this signal can be objectively analyzed. Optical methods of monitoring tissue, or invasive methods without optical diagnostics, are taught in U.S. Pat. No. 4,290,433, U.S. Pat. No. 4,622,974, U.S. Pat. No. 4,945,895, U.S. Pat. No. 5,030,207, U.S. Pat. No. 5,131,398, U.S. Pat. No. 5,271,380, and WO 92/17108. Each of these does not perform a tissue analysis, requires fluid or tissue removal or sampling, utilizes fluorescence or other emission-based techniques which measure light other than that used to perform the illumination, is restricted to external or penetrating use, or does not teach tissue classification or identification. Automated classification of tissues for general clinical use via light in vivo has not been taught, nor has such a tool been successfully commercialized.

SUMMARY AND OBJECTS OF THE INVENTION

The present invention uses optical methods to allow for a rapid tissue diagnosis via characterization of tissue in an automated manner. The present invention relies upon the optical characteristics of tissue, either by variations in absorbance or scattering by wavelength or over space, in order to make a medical diagnosis, namely an optical classification of the tissue by tissue type or state, either as a present/absent decision, as a localization, or as an image.

A salient feature of the present invention is an incorporation of the observation that light, while both being scattered and absorbed by scattering media, can be made to penetrate human tissue, then be detected upon reemergence in order to allow quantitation of characteristics of the interior of the tissue, such as tissue types or biochemical composition, imaging and localization of tissue types, and that such information is medically useful.

Accordingly, an object of the present invention is to provide a method for detecting the presence of tissue types using light, whether to merely detect, classify, localize, or image the tissue.

A second object is that classification of the tissue can be made, wherein the classification can be selected from normal tissue types (such as artery, vein, nerve, lymph, liver, muscle, brain, gray matter, white matter, colon, blood), from tissue components (water, fat, hemoglobin), from tissue states (frozen, thawed, coagulated), from tissue functional status (alive, dead, at risk for dying), and that such classifications can even be used to determine tissue pathology (normal or abnormal).

A third object is that localization of tissue by type can be made, such that the tissue may be classified as present or absent, distances from one tissue to a reference point can be measured, or the tissue can be localized in space. A measurement that characterizes a tissue at a defined point in space is considered imaging. This spatial distribution can be key in medical diagnosis.

Another object is to provide a noninvasive method for optically detecting, quantifying, or imaging a change in the tissue state, whether to merely detect, classify, localize or image the change in the tissue. This change in state can be in response to a medical intervention, such as a change in the blood volume of the motor cortex of the brain during muscle activity, or the tool itself can initiate the change, such as by squeezing the tissue to assess vascular responsiveness, or freezing, thawing, welding, denaturing, or otherwise affecting the tissue.

Another object is that this technique is not limited to monitoring the tissue from the outside (e.g., such as is commonly done in computed x-ray tomography), but also may be used to allow a probe to measure its surrounding medium, such as if an optical fiber is inserted into a cyst, to allow sizing and diagnosis of the cyst from the inside, or if an underwater probe is to take note of objects nearby, such as rocks, when the water is cloudy, to allow better guidance. Thus, such an approach can be used both to detect changes within a medium, as well as around a probe submerged in a medium that comprises the environment of the detection apparatus. This method has the advantage of being noninvasive, should this be desired, or invasive, should measurement inside the tissue be useful. For example, the characterization of tissue as a probe is advanced through the tissue can be important in diagnosis and localization.

Another object is that any medical probe can be modified to perform this classification function, such that measurements may be made using existing medical equipment, modified to hold emitter and detector elements, such as modified hand-held medical probes, tips of surgical tools, stethoscopes, EKG leads, or other devices. The ability to classify can also be designed into new or unforeseen medical probes or devices. This function can be incorporated into replaceable device tips.

Another object is that the classification can be enhanced by a priori knowledge, such as the spectral characteristics of target tissues (which can be stored for reference in the device or in the probe), the area of the body the physician is working (such that far away tissues need not be considered in the analysis), or other medical scans (such as a CT or MRI scan).

Another object is that this data can be enhanced by collection over time. In many medical applications, the value of a measurement is enhanced by determination of temporal characteristics. For example, the detection of an enlarging bleed in head tissue holds a different significance than the detection of a stable, but otherwise similar, bleed. In underwater applications, the ability to detect moving nearby objects may also be important. Subtraction of the data at one point in time from data collected at a second point in time allows elimination of many types of individual tissue variations, and can yield improved data.

Another object is that this classification represents a decision point upon which a human response may be initiated, such as with an alarm bell, or an interlock decision may be initiated, such as via an output signal attached to a medical device. A final object is that the detection, localization, or imaging information can be presented to the user in a number of ways, such as an image of object location or even an image of characteristics of the medium such as absorbance, in such a manner as to allow the user to gain an incremental understanding of the presence or location of inhomogeneities in the medium, or even an understanding of characteristics of the medium itself.

There is provided a diagnostic monitor for classifying biological tissue in which a light emitter is optically coupled to the tissue to be diagnosed and a light detector is optically coupled to the tissue to detect a portion of the light which passes through the tissue. The tissue classifier receives a signal from the detector and provides an optical classification output signal. A method of classifying tissue is also described. The breadth of uses and advantages of the present invention are best understood by example, and by a detailed explanation of the workings of a constructed apparatus, now in operation. These and other advantages of the invention will become apparent when viewed in light of accompanying drawings, examples, and detailed description.

BRIEF DESCRIPTION OF THE DRAWINGS

The file of this patent contains at least one drawing executed in color. Copies of this patent with color drawings will be provided by the Patent and Trademark Office upon request and payment of the necessary fee.

The following drawings are provided:

FIG. 10A–10D schematically show an a nearby object classified in a tissue model as an optical image, a numerical distance-to-object, and a graph of object presence versus depth.

DEFINITIONS

Figure 1:
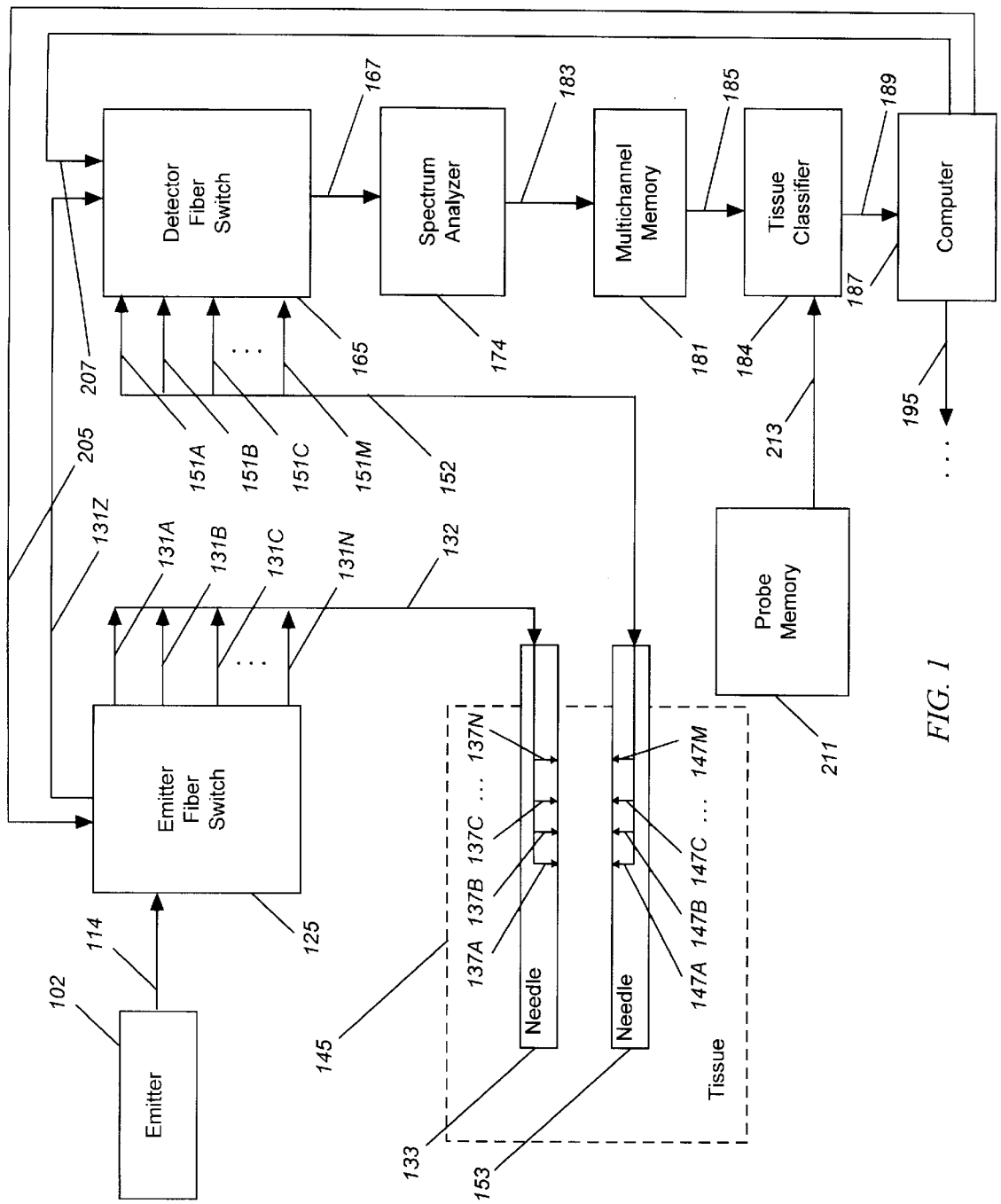
FIG. 1 is a schematic diagram of a monitor for classifying biological tissue in accordance with the invention.

For the purposes of this application, the following definitions are declared:

Classification of Tissue

A tissue classification implies an automated processing of the raw information contained in the usual medical image or measurement (such as shadows from bones) into a quantitative parameter or decision about the tissue, such as a classification (e.g., "is this a hemorrhage?") or a localization or a classification (e.g., "how far is the frozen tissue from my probe"). A classification of tissue can be into a tissue category by type, such as nerve, artery, vein, lymph node, hemorrhage, or by tissue state, such as frozen, denatured, coagulated. A localization of the classification can be as a distance, as an image (e.g., "where is the stroke"), or even as a characterization of a tissue at a point in space (e.g., "what is the type of tissue located exactly 4 cm below this probe?").

Light

The electromagnetic radiation used is intended to be between 10 nm and 100 microns in wavelength, but includes any radiative wave in theory.

Tissue

Living tissue or tissue-like radiation-scattering media, such as skin, brain, bone, or even cloudy water.

Light Emitter

A probe that emits light. It may be composed of a simple light bulb, a laser, a flash lamp, or another light source or combination of sources, or it may be a complex form including a light source, a transmission element such as an optical fiber, a guidance element such as a reflective prism, and other elements intended to enhance the optical coupling of the light from the emitter to the skin or tissue under study. The light source may be continuous, pulsed, or even analyzed as time-, frequency-, or spatially-resolved. The emitter may consist of a single or multiple light emitting elements.

Light Detector

A probe that detects light. As above, it may be single or multiple, simple or complex. The detection may be performed in reflectance or in transmission.

Optical Coupling

The arrangement of a light emitter (or light detector) in such a way that light from the emitter (or detector) is transmitted to (or detected from) the tissue. This may include the use of optical elements such as lenses, collimators, concentrators, collectors, optical fibers, prisms, filters, mirrors, or mirrored surfaces. Optical fibers have two ends, which are generally interchangeable, and are referred here as the entrance end if the light is generally entering the fiber, and as the exit end if the light is generally leaving the fiber.

Regional Inhomogeneity

An object or tissue that varies from the surrounding tissue in an optically distinct manner. For example, a blood vessel in a muscle is a regional inhomogeneity, as is a stroke in a normal brain.

Optical Path Effect

An effect of the tissue on the path of light taken through the tissue. Such changes in path can be induced by changes in scattering or absorbance at one or more wavelengths, and can be monitored in part by measuring reflectance, scattering, or absorbance, or any feature of the detected light that is affected by changes in these quantities.

Optical Biopsy

An optical characterization of tissue.

Imaging

The classification of a region of space in at least zero dimensions. An example of a zero dimension scan is the use of more than one point measurements on the surface of the scalp in order to determine the oxygenation of a specific, deeper portion of the brain, such as the gray matter, at one point in space or over one region in space. A one-dimensional scan could be the display of the presence of a certain tissue type, such as glandular tissue in the uterine wall, as a function of depth, as shown in Example 8, below. Two-D and 3-D scans are standard radiological views, and are well-known, as shown in Examples 2, 4, 6, and 7. A 4-D scan could include the three spatial dimensions x, y, and z, as well as time t.

Quantitative Parameter

A measurement that can be quantitatively measured, such as a classification of tissue by type, or the distance of a type of tissue from the measuring probe.

DESCRIPTION OF A PREFERRED EMBODIMENT

One embodiment of the apparatus will now be described. In the device shown in FIG. 1, light is emitted by emitter 102 (Mini-Maglite™ Krypton miniature bulbs, Mag Instrument, Torrance, Calif.), and travels down optical fiber 114 to emitter switch 125 (Model GP-700, DiCon FiberOptics, Berkeley, Calif.) which directs light to one of N fibers 131A to 131N (200 $\mu$m core glass fibers with cladding and buffer, Purdy Electronics Corp., Sunnyvale, Calif.). Alternatively, the light source, such as a surface mount LED, could be placed directly on the probe and electronically switched. Reference fiber 131Z, connected to switch 125, bypasses the tissue for use in monitoring the optical characteristics of source 102. Illumination fibers 131A to 131N connect to fiber bundle 132 which passes into first needle 133 that extends into tissue 145. Light from bundle 132 passes through first needle ports 137A to 137N, containing fibers 131A to 131N respectively, and into tissue 145. Light traveling through tissue 145 is collected through second needle ports 147A to 147M by collection fibers 151A to 151M, respectively, passing as fiber bundle 152 from second needle 153, offset a small distance from first needle 133. Light from one of collection fibers 151A to 151M, or from reference loop fiber 131Z, is chosen for monitoring by detector switch 165. Output fiber 167 from detector switch 165 is connected to spectrum analyzer 174 (Ocean Optics Spectrophotometer, Model PS1000, Dunedin, Fla.), which records the light, and transmits an electronic signal to be stored in multichannel memory 181 (A/D-converter board Model PCM-DAS16/330-1, Computer Boards Inc., Mansfield, Mass.) via cable 183. Multiple spectra can be stored in Memory 181, allowing for collection of standardization spectra for correction of the spectra for instrument response, and also allowing for multiple regions of the tissue to be sampled and later compared. Spectra stored in memory 181 are then classified by tissue classifier 184 (in this case, a computer configured so as to perform tissue classification, AMS Laptop Pentium™ 120 MHz computer, Model AMS SY19-T40177 Travel Pro 1900, available through Ocean Optics, Dunedin, Fla.) after transmission over cable 185, and the result is passed to computer 187, which collects and processes the identified tissue types, via cable 189. Processing of the identified tissue types by computer 187 may consist of the computation of a graph or image, or the calculation of a number, such as a distance. The result of this calculation is output 195. Further, emitter switch 125 and detector switch 165 are under the control of computer 187 via cables 205 and 207, respectively, to allow for control of the data collection. Computer 187 may be a different computer than that used in classifier 184, or the same computer may be used for both functions. Note that reference fiber 131Z allows calibration of light emitter 102, and that such calibration information may be stored in memory 181.

Alternatively, or in addition, a reference database may be stored as an internal database within memory 181 or contained within programmable probe memory 211 and transmitted to classifier 184 via probe cable 213 for use in classification. The reference database contains various information needed to make classifications, such as key features used to discriminate known tissues or a library of characteristic signals from previously identified tissues. Information in this database may then be used by classifier 184 in making tissue classification decisions using standard methods (least squares fits, partial components regression, neural networks, etc.).

Operation of the device is now described. First, the instrument response is determined, in order to produce an instrument response baseline. The probe is submerged in a vial containing 1 L of 20% fat-emulsion (Liposyn-II™ 20%, Abbott Labs, Chicago, Ill.), which scatters light, but does not absorb significantly save for the water spectrum absorbance. Emitter switch 125 directs light to fiber 131A, while detector switch 165 collects light from selected collection fiber 151A. Such spectra, collected between the two needles and across a scattering sample using particular emitter-detector fiber pair, are called sample illumination spectra. Emitter switch 125 then directs light to fiber 131Z, while detector switch 165 collects light from fiber 131Z. Such spectra, collected from the light source without intervening tissue, are called source illumination spectra. Last, the light source is turned off, and the measurements from fiber pair 131A and 151A, and the measurements across fiber 131Z, are repeated without emitter fiber 114 illuminated. These non-illuminated spectra represent the background detector signal in the absence of illuminating light, and are called sample and source background spectra, respectively.

Using well-known methods, the sample and source background spectra are subtracted from the sample and source illumination spectra, respectively, thus removing the background light counts and producing background-corrected spectra. Next, each intensity point in the background-corrected source spectra are divided by the corresponding intensity point in the background-corrected sample spectra, to produce a series of raw sample spectra. In this case, in which the sample is a white-appearing scattering fluid without significant non-water absorption of light, the raw sample spectra represent the instrument response, and correspond to the spectra seen by the each emitter-detector pair in the probe in the absence of any real non-water absorbance features. Alternatively, a scattering sample without any water present can be used as the standardizing fluid if the detection of water absorption in the sample is important. These instrument response spectra are saved in memory 181. All future spectra in this experiment will now automatically be divided by the corresponding instrument response spectrum to produce a set of final sample spectra corrected for instrument response. After all measurements have been completed from emitter fiber 131A, this process is then repeated for the same or other pairs of selected emitter fibers 131A to 131N and detector fibers 151A to 151M.

To test the instrument response calibration performed above, the lipid is now remeasured using the same steps listed above, to produce a second set of raw sample spectra. Next, each intensity point in these second raw sample spectra are divided by the corresponding intensity points in the saved instrument response spectra, to produce a set of final sample spectra. In this case, the raw sample spectra set and the instrument response spectra set should be similar, and thus the division of one by the other should produce an intensity of one, or nearly one, in all channels measured. Each final sample spectrum, therefore, should be flat, with an absorbance, A, defined as $A=\log_{10}=$(instrument response intensity)/(sample residual intensity) equal to zero, or nearly zero, at all points. Other types of spectra analysis, including differential spectra, normalization, and other corrections can be made within the spirit of this invention.

Once the device is corrected for instrument response, a sample tissue can be measured. To test the sample, penetrating needles 133 and 153 are placed into the tissue, as described earlier, and pairs of fibers, in this example 131A/151A, 131B/151B, . . . 131N/151M are scanned, though other scanning arrangements may be desirable for other applications. For each fiber pair scanned, a source spectrum is also collected through fiber 131Z to correct for changes in source intensity and spectrum, and then each sample spectrum is corrected for instrument response as described above, to generate a series of final sample tissue spectra. The result is a set of spectra at different depths or locations in the tissue, and are stored in memory 181.

Next, each corrected spectrum is passed to classifier 184, where it is analyzed by tissue type. The result of this analysis and classification is passed to computer 187, producing output 195 as a result. This result may be a diagnostic classification (such as the presence or absence of a specific tissue type as shown in Example 1), a table (such percentage of a type of tissue by depth as shown in Example 8), a graph (such as the presence or absence of a tissue type over time as shown in Example 3 or a distance as shown in Example 5), a number (such as the distance to an object as shown in Example 5), an image (such as the location of a stroke as shown in Examples 2, 4, 5, 6, and 7), or a localization (such as a measurement of distance as shown in Example 4).

A discussion of the classifier now follows. In this preferred embodiment, classification by classifier 184 is performed by a computer, constructed with analysis routines, and arranged so as to provide a classification of tissue. However, the tissue classifier can be a calculator or other device configured so as to provide tissue classification output. As noted above, computer 187 may be a different computer than that used in classifier 184, or the same computer may be used for both functions.

Analysis methods used by the classifier may involve spectral features, such as peak wavelength, slope of a spectral region, or the first, second, or higher order differentials of the spectrum. Such methods of analyzing spectra are known, and methods exist for removing background signal or scattering effect, or in emphasizing low-concentration substances such as glucose or cytochrome. Methods of analysis include principal components regression (e.g., Pirouette, Infometrix, Seattle, Wash.), least squares multivariate fits (SigmaPlot, Jandel Scientific, San Rafael, Calif.), neural networks (e.g., BrainMaker, California Scientific Software, Nevada City, Calif.), and the like, all of which are well known to those skilled in the art. For example, one method of such classification would be to use a neural network. In this method, the network is "trained" using a series of spectra from known tissues, and then the network is "queried" by giving the network the unknown spectrum and asking the network to classify the tissue. Such methods of mathematical analysis are known, and many different classification methods can be developed by those skilled in the art within the scope of the present invention. Optical path effects can be measured, such as mean photon distance traveled, or the like, as taught in time-resolved or frequency-resolved methods. Identification may be improved by using a computational comparison to set of reference criteria (spectra or features of the spectra such as the first differential of the spectrum), rather than a simple ratio, in order to arrive at a determination. Such reference values may be updated over time as better understanding of the meaning of the spectra is reached, and may even be built into the sensor itself, such that each sensor comes calibrated for a certain tissue set or for a certain diagnostic procedure. Similarly, identification could be improved by background correction and correction for the instrument response function, as is well known in the art. The known approaches for spectral analysis fall within the scope of the present invention whenever they are used to classify tissues by type within a scattering medium such as human tissue. Such analysis and classification may allow for a chemical analysis of the tissue, allowing resolution of the optical data into concentrations of hemoglobin, water, fat, etc. Such identifications may be used to identify tissues in the body, such as nerve, artery, vein, lymph node, and muscle.

Figure 2C:
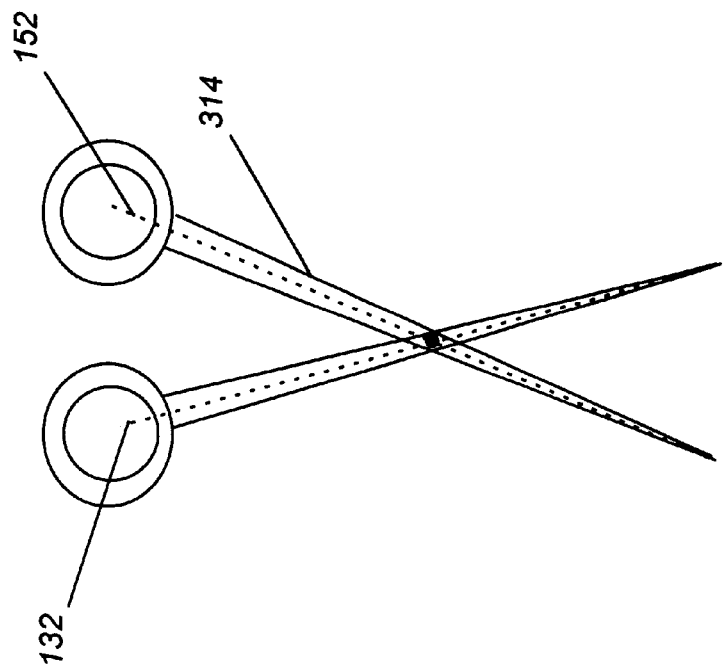
FIGS. 2A–2E are examples of probes which can be used in the monitor as shown in FIG. 1.
Figure 2A:
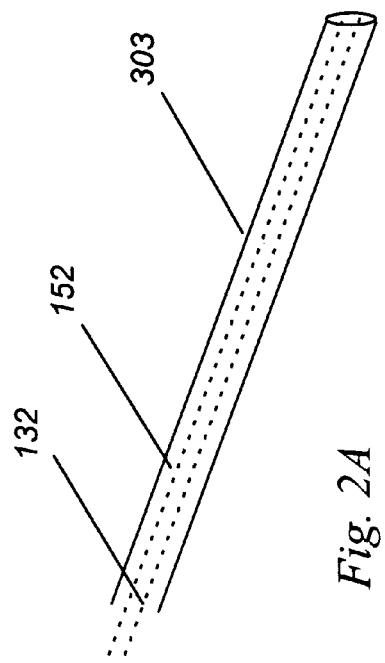
Figure 2B:
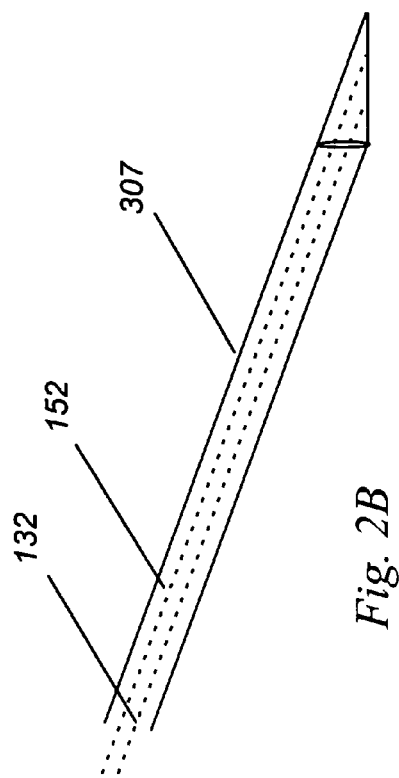
Figure 2D:
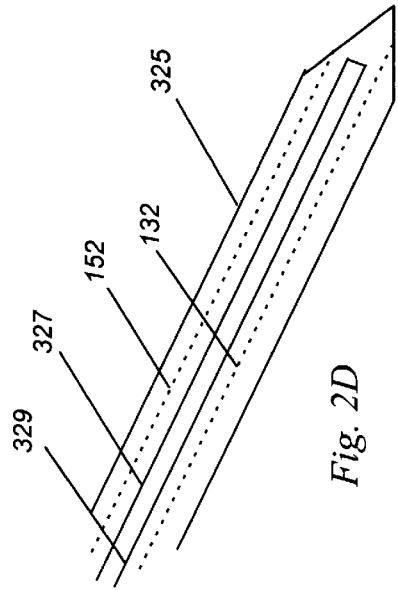

The configuration of the probe and probe construction are important. For example, it may be essential to have the fibers stabilized with respect to the tissue, to assist in the measurement. Some examples are shown in FIGS. 2A though 2E. Emitter bundle 132 and detector bundle 152, containing fibers 131A to 131N, and 151A to 151M, respectively, can be held in place by incorporation into the body of medical probe 303 (FIG. 2A), into surgical tools such as knife 307 (FIG. 2B) or grasper 314 (FIG. 2C), or into another structure which holds the fibers in a desired optical contact with the tissue to be measured. The probe may be designed to act upon the tissue in a defined way, such as cryoprobe 325 (FIG. 2D) that monitors tissue as it freezes the tissue with a cold liquid nitrogen source flowing into input pipe 327 and out through output pipe 329.

Figure 2E:
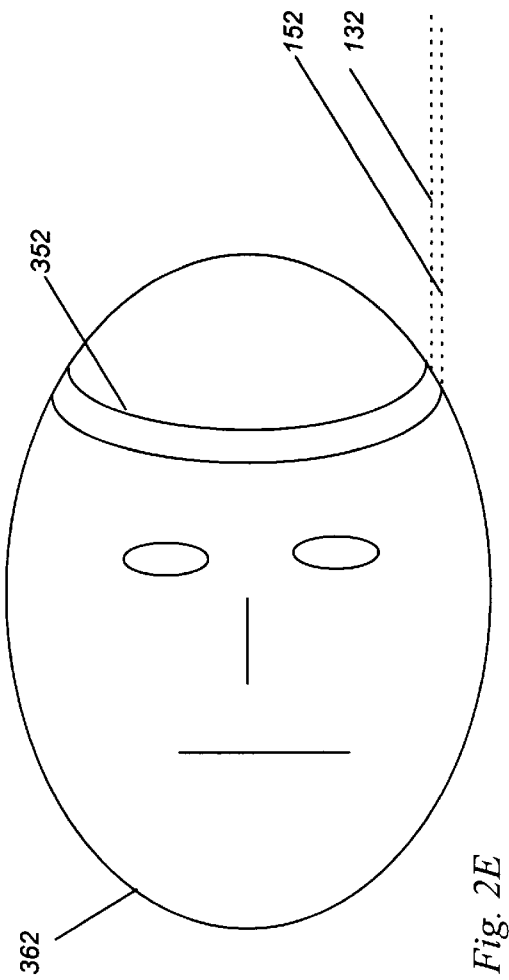
Figure 3A:
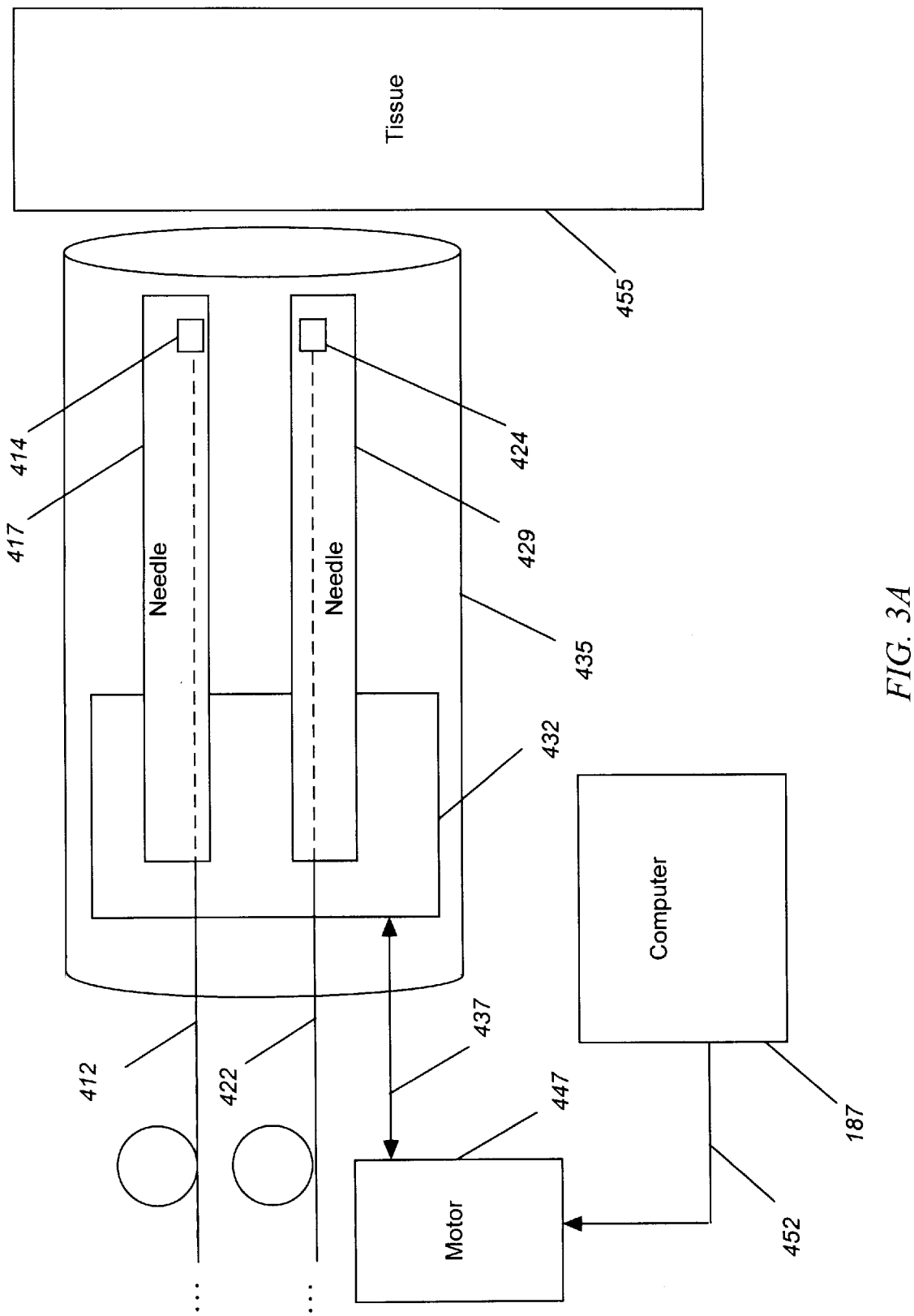
FIGS. 3A–3B show a probe which can be used for minimally invasive diagnosis.

A probe can be noninvasive or invasive. First, a probe may be constructed to image from the surface of the tissue, rather than penetrating the surface of the tissue. For example, emitter fibers 131A to 131N and detector fibers 151A to 151M may be woven into headband 352 and wrapped around a tissue, such as head 362 (FIG. 2E). From such a surface probe, an image can be reconstructed using imaging algorithms that are known. This image can then be further processed by tissue type, using the present method. Alternatively, a probe can be automated to invasively sample at different depths as it is pushed into the tissue. This simplified probe requires only one emitter and one detector, and depth is estimated by the fractional time passing between entry and full insertion, with the speed of the probe assumed to be constant during insertion and sampling. Alternatively, the probe can be motorized and move into the tissue in defined amounts, such that the depth of the probe at each sample is precisely known and under device control. In this case, shown in FIGS. 3A and 3B, emitter fiber 412 is connected to prism 414 (1 mm×1 mm×1.4 mm hypotenuse-mirrored prisms, Reynard Corporation, San Clemente, Calif.) inside emitter needle 417, and detector fiber 422 is connected to prism 424 inside detector needle 429. Needles 417 and 429 are mounted in sliding base 432, contained within tubular sleeve 435. Base 432 is moved back and forth within sleeve 435 whenever sliding cabled wire 437 is pulled back and forth by motor 447 (Super Vexta Model PH264-01, Oriental Motor Co., Tokyo, Japan), much as a remote cable release for a camera operates a distant camera shutter when the cable release is pushed or released. As shown in FIG. 3A, motor 447 is controlled by computer 187 over electrical cable 452. Extending base 432 moves needles 417 and 429 into tissue 455, as shown with the needles extended deep into tissue 455 in FIG. 3B; retracting base 432 pulls needles 417 and 429 out of tissue 455, as shown with the needles retracted out of tissue 455 in FIG. 3A. This results in a small probe that can be passed through the cervix. Motor 447 and cabled wire 437 could be replaced by other mechanisms, such as a fluid controlled ratchet, or other mechanical or electrical device obvious to those skilled in the art of mechanical engineering.

Figure 4:
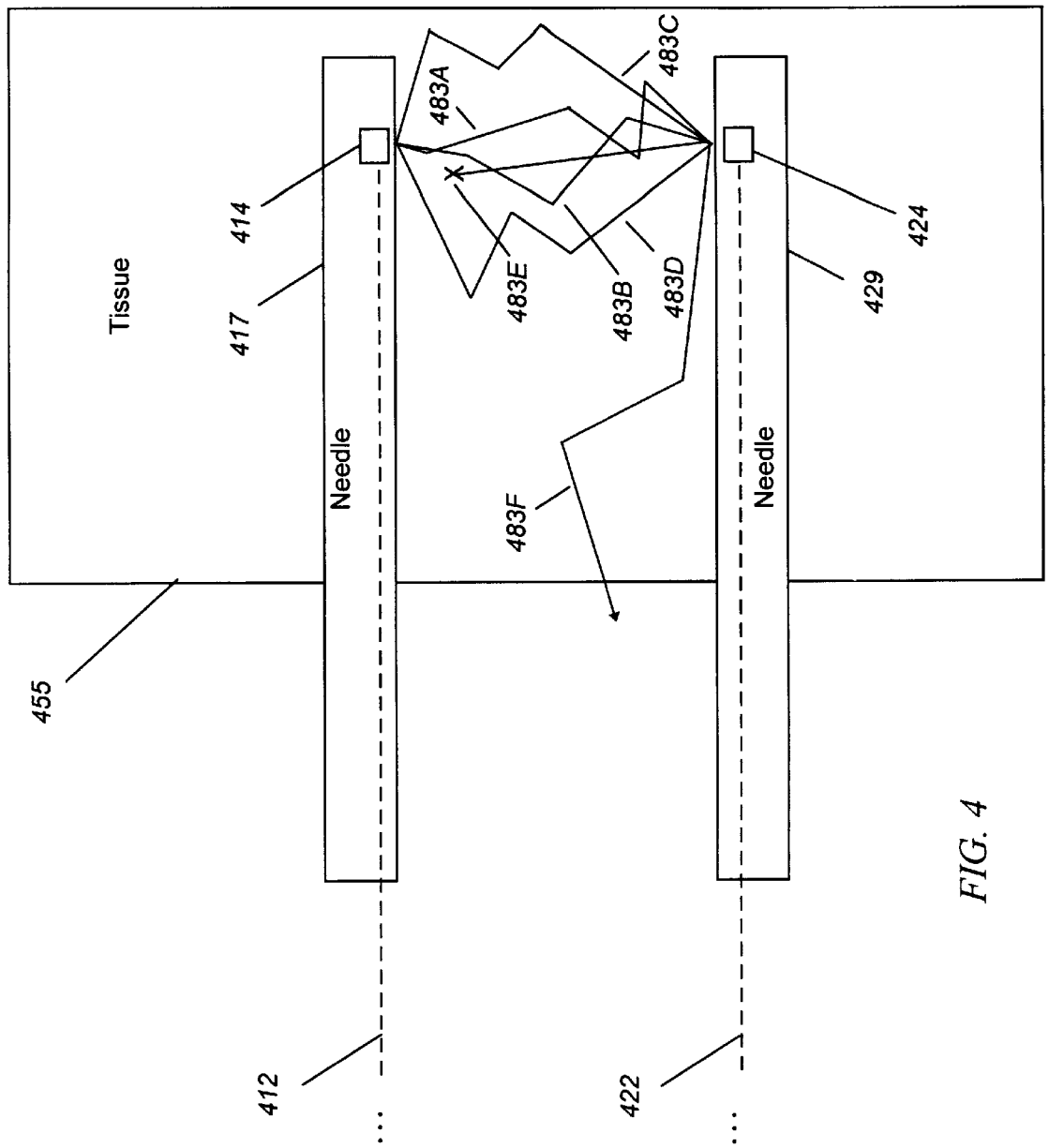
FIG. 4 schematically shows typical photon paths through the tissue.

Of note, when needles 417 and 429 penetrate into tissue 455, the photons traveling between needles 417 and 429 take a wide range of paths, as shown in FIG. 4. Some photons may take relatively direct paths, such as paths 483A and 483B, while others take longer paths that stray far from the direct visual line between emission at prism 414 and collection at prism 424, such as paths 483C and 483D. Still, others stray along lines that result in absorbance, such as path 483E, or escape from the tissue, such as path 483F, and never can be collected. This range of paths is due to the scattering of light by tissue, in which an emitted ray of photons turns into a diffuse glow as the original directionality of the photon beam is lost, which destroys standard optical imaging clarity, similar to photons becoming randomized in a fog leading to the images of far-away objects becoming obscured. The present device takes advantage of this effect as the scattering provides an averaging and volume sampling function. When detected illumination is measured after it has propagated through the tissue over substantially non-parallel multiple courses taken through the tissue between the time the photons are emitted and then detected, many regions of the tissue can be sampled, not merely the tissue on a narrow line between emission and detection. This allows a small but important characteristic tissue from being easily missed if it happens not to be directly between the emitter and detector. As a result, the detected light in the present invention is comprised of multiple regional component signals, each regional component signal comprised of radiation having propagated through a different region of the tissue.

EXAMPLES

The breadth of uses of the present invention are best understood by example, eight of which are provided below. These examples are by no means intended to be inclusive of all uses and applications of the apparatus, merely to serve as case studies by which a person, skilled in the art, can better appreciate the methods of utilizing, and the scope of, such a device.

Example 1
Classification of Tissues By Type

Figure 5:
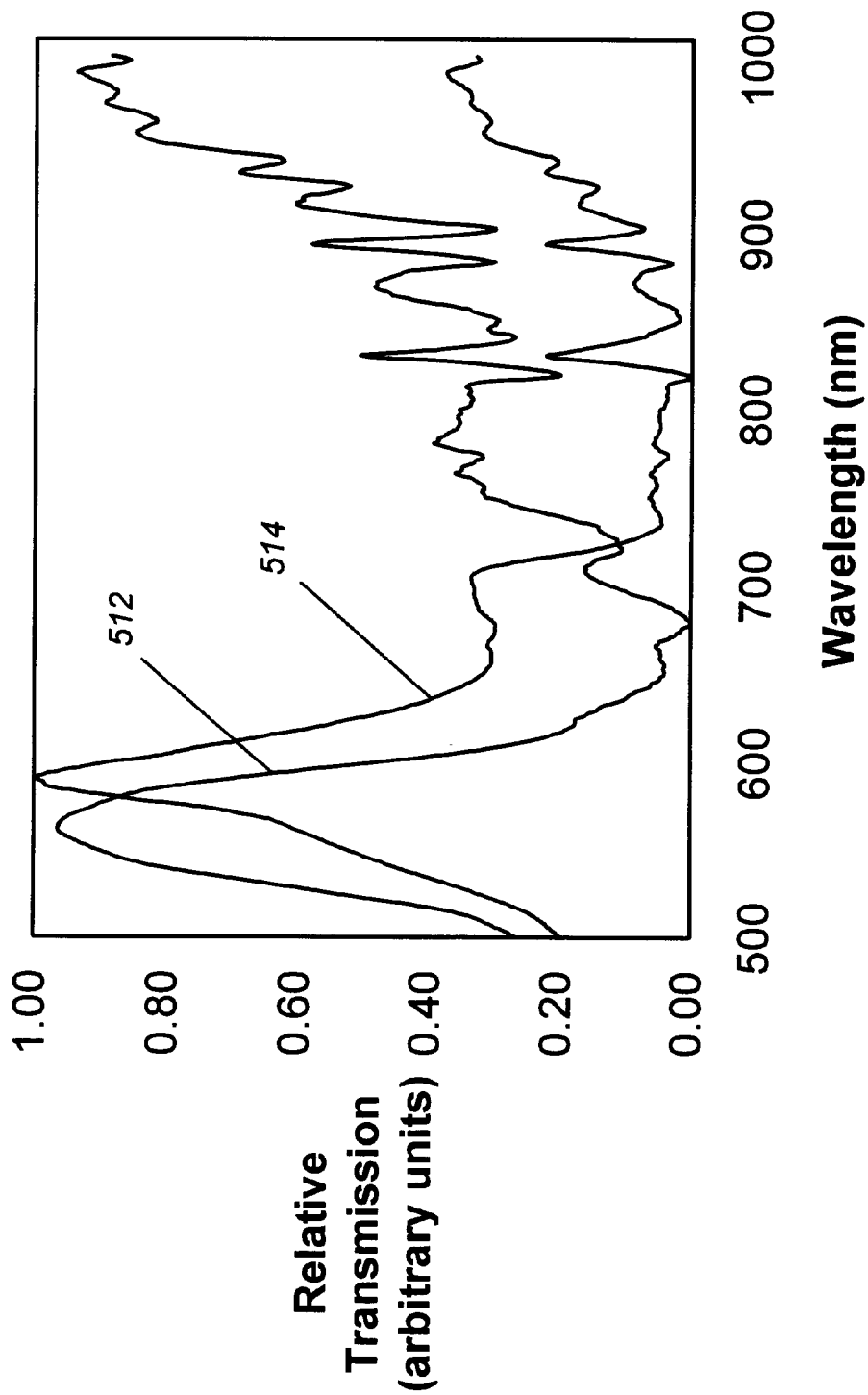
FIG. 5 shows the optical spectrum of two sample tissues.

Tissue classification can be used to recognize different tissue types. In this experiment, different tissues were measured using the device similar to that shown in FIG. 1, and light was collected from one emitter and detector pair. Optical spectra from muscle and fat are shown in FIG. 5. There are distinct differences in spectra between each tissue shown, for example between muscle 512 and fat 514. These differences allow for a simple discrimination between the tissue types, and several algorithms can be selected to classify the tissue. In this case, the algorithm could be as simple as:

a) if the absorbance peaks at a wavelength over 575 nm, then tissue is fat; or, b) otherwise, the tissue is not fat.

This method requires use of the entire collected spectrum in order to identity a peak wavelength. The classification is performed by a computer-based classifier, such as classifier 184 in FIG. 1. A more complex algorithm could use the ratio of absorbance at two wavelengths, for example at 675 nm and 800 nm, where the ratio of $A_{675}/A_{800}$ is used as follows:

| Ratio | Classification |
|---|---|
| 0.00–0.02 | Unknown |
| 0.02–0.10 | Muscle |
| 0.01–5.0 | Unknown |
| 5.0–7.0 | Fat |
| 7.0 and up | Unknown |

This latter method requires only two wavelengths, allowing for simple light sources such as two wavelengths of surface-mounted LEDs, rather than a broad spectrum source, and a simple light detector, rather than a more complex spectrophotometer. Again, the act of classification is performed by a classifier, such as classifier 184 in FIG. 1.

Example 2
Classification of Tissue Types as an Image

Optical methods can be used to perform imaging (Benaron, U.S. Pat. No. 5,413,098). Tissue classification criteria, taught in the present invention, can then be applied to such images. In this example, image classification has been used to process an optical image of tissue, and then to classify for the presence of a bleed in the brain, or hemorrhage, in the brain of an infant.

Figure 6:
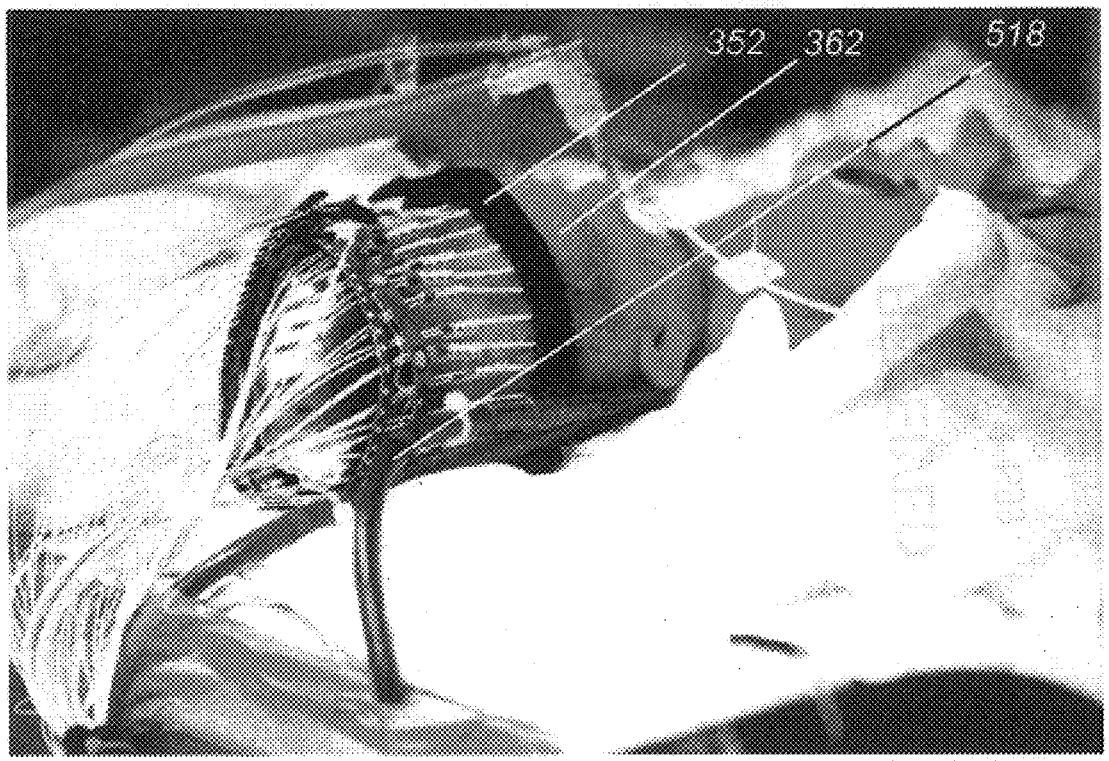
FIG. 6 shows an imaging headband mounted on an infant's head.
Figure 7:
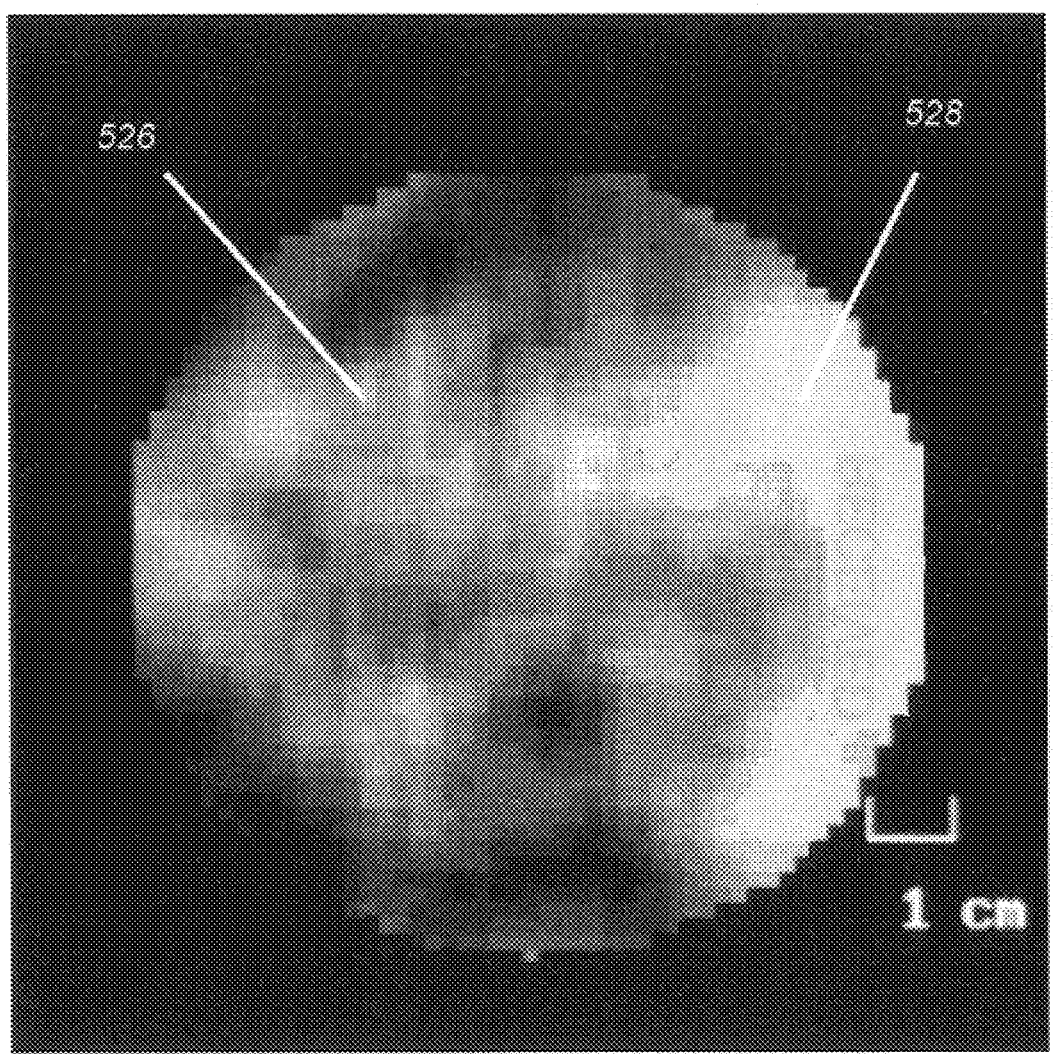
FIG. 7 is a photograph of a classified optical image of brain hemorrhage obtained with a monitor constructed in accordance with the present invention.

To generate this image, we optically monitored the head of a living infant at risk for bleeding using the device shown in FIG. 1 attached using optical headband 352 wrapped around head 362, shown schematically in FIG. 2E and photographically in FIG. 6. Note that in FIG. 6, the infant is receiving heart/lung bypass, so that the oxygenation of the blood leaving the brain can be directly measured by sampling blood from bypass tube 518. Optical image 526 in FIG. 7 was tomographically generated from the optical data collected using the method and device of U.S. Pat No. 5,413,098. Next, the data was classified using the approach of the present invention by identifying areas with an absorbance more than 1 event per centimeter ($\mu_a > 1$ cm$^{-1}$), consistent with an area having a high concentration of blood, thus localizing brain hemorrhage 528 (yellow) in optical image 526 (gray). Note that the optical classification was based upon an automated classification analysis. This optical approach may be medically important, as bleeding in the brain in premature infants can lead to brain injury or excess fluid accumulation and pressure build-up, and is a major cause of morbidity and mortality in those infants. Other identifications could be made, allowing localization of gray matter, white matter, spinal fluid, and the like.

Example 3
Classification for Detection of Changes in Tissue State

In this example, a change in the state of the tissue is monitored. Freezing, a change of tissue state, can be detected using changes in the optical characteristics of the tissue. The detection of freezing in a turbid liquid may be important in the monitoring of materials which must be frozen, such as with biologic samples. It may also be important to be able to detect when freezing has been completed, such as use of an optical device to verify that poultry has been fully frozen, in order to minimize time of freezing before removal from a freezing bath, or that human tissue has been adequately frozen during a procedure known as cryosurgery. In cryosurgery, treatment of a cancer or other lesion is achieved by freezing the tumor using a liquid nitrogen filled needle stuck into the tumor. This allows killing of the tumor without having to cut up tissue in order to remove it. This is important if the tumor is in an critical location in an important organ, such as the brain or liver. However, it can be difficult to detect when the correct amount of freezing has occurred. If too little tumor tissue is frozen, then the tumor lives and the treatment is ineffective, if too much tumor tissue is frozen, then complications may arise due to the injury of healthy tissue and blood vessels through the freezing process. Thus, localization of the extent of freezing, and not only detection of freezing, can be crucial to a patient's health.

Figure 8A:
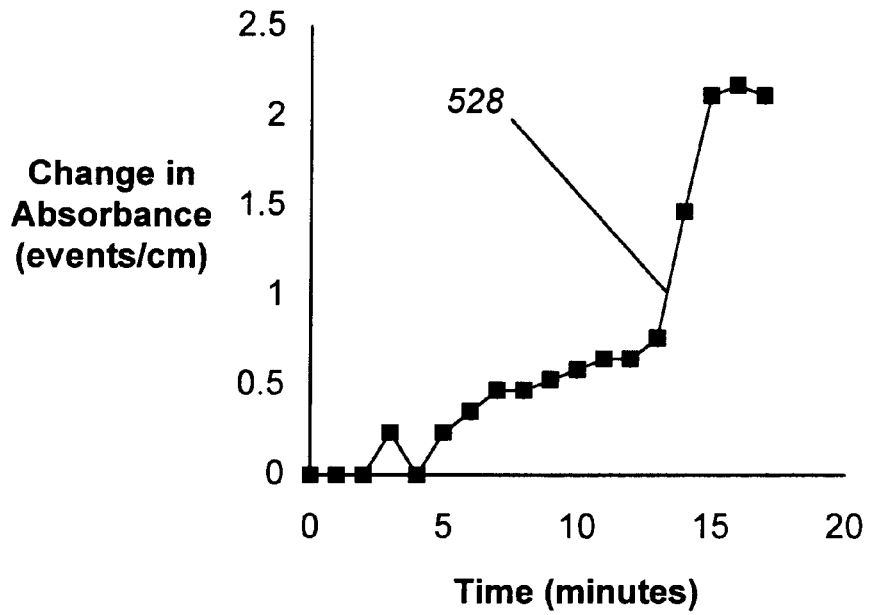
FIGS. 8A–8B illustrate the optical detection and classification of freezing in tissue.
Figure 8B:
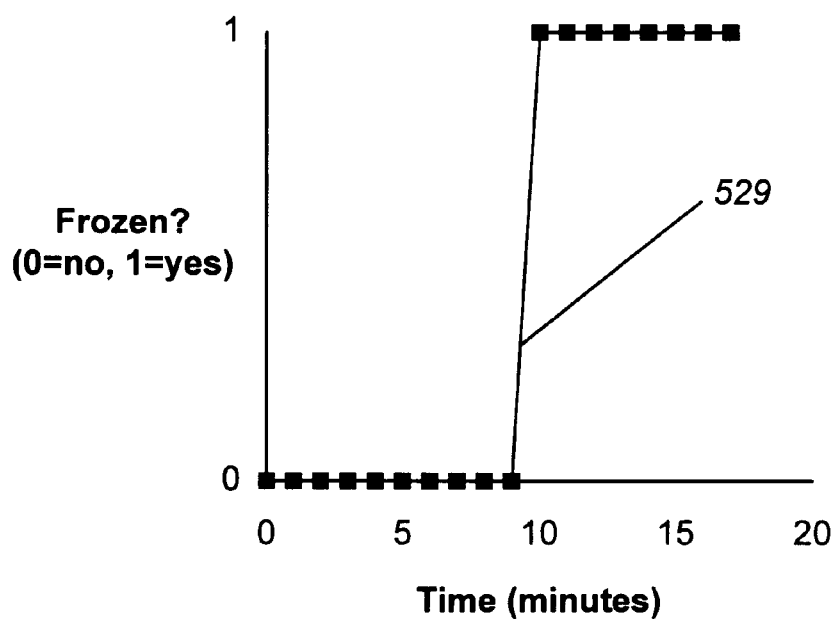

In this example, chicken breast, initially at room temperature, was frozen using a liquid-nitrogen cooled probe, and the changes during freezing were monitored using device similar to that shown in FIG. 1 and a probe similar to that shown in FIG. 2A. The initial average absorbance at all wavelengths measured (400 nm to 1100 nm) was recorded, and used as the baseline value of absorbance. Changes in average absorbance were recorded, producing absorbance graph 528 in FIG. 8A. As tissue freezes, the scattering of light increases greatly, and therefore the amount of light reaching the detector falls. This fall in detected light is recorded as an increase in absorbance. A classification algorithm was developed, in which "frozen tissue" was defined as tissue with an increase in absorbance of greater than 0.55 events/cm, and an automated classification was used to produce the classified output of frozen versus not frozen graph 529 in FIG. 8B. Other, more sophisticated algorithms could be developed, if needed, but in this case a simple algorithm for classification suffices.

Such changes in path or spectrum (an optical path effect) can be used to follow the welding of tissue using lasers, or the treatment of tumors using cryosurgery. Similarly, such an approach can be used to monitor the heating of tissues. Warming of tissue is used to weld tissue and to kill tissue, such as during laser welding or electrocautery Feedback as to when the tissue is correctly denatured would be of use in these approaches.

Example 4
Classification for Imaging of Changes in Tissue State

Figure 9A:
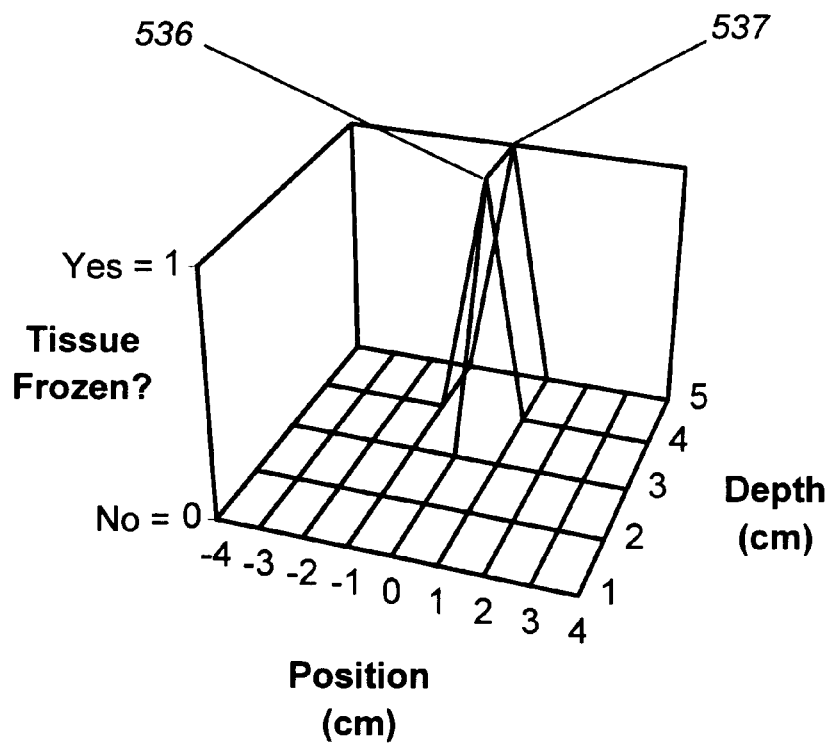
FIGS. 9A–9B graphically show data used to construct a classified optical image of tissue freezing.
Figure 9B:
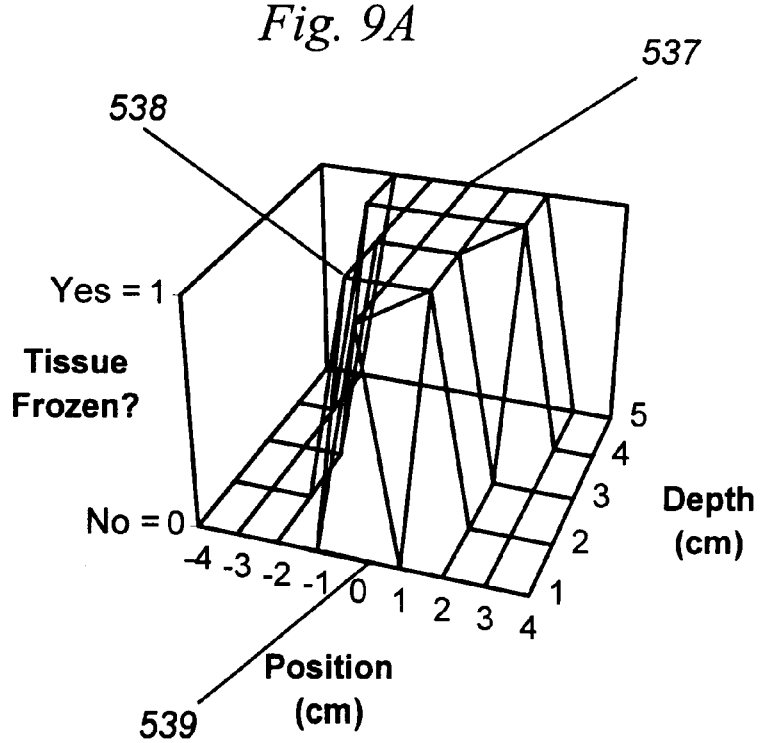

In this example, we demonstrate the ability to image freezing in chicken meat, recorded by measuring local increases in absorbance, associated with the increased scattering seen in tissue undergoing freezing, at multiple fiber locations. Photons were transmitted into chicken meat initially at room-temperature and enclosed in a thick-walled Plexiglas™ holder, with an internal tissue cavity measuring 16 cm (x) by 16 cm (y) by 3 cm (z), and packed with whole chicken breast. Pressurized liquid nitrogen, supplied by a tank used in actual cryosurgery, was passed through an 0.5 cm probe, such as that shown in FIG. 2D, passing through the chicken sample in the z-axis. A series of surface emitter and detector fibers were used to scan at a series of locations approximately 4 cm from the freezing probe. Classification of "frozen" versus "not frozen" was computed as in Example 3, above. These classifications were used as input into an imaging algorithm, producing a sequence of images, two of which are shown in FIG. 9A and 9B. In these images, an area of freezing can be classified and localized. Initially, as shown in FIG. 9A, the area of freezing measured a few minutes after the start of freezing is at point 536, at a depth of 5 cm and a position offset of zero cm, which is near freezing probe location 537. Later, as shown in FIG. 9B, the freezing front advances to point 538, at a depth of 1 cm and a position offset of zero cm, which is much farther from the probe and approaching tissue edge 539.

A long series of emitter and detector fibers can be placed into needles, or similarly into catheters, to perform such imaging of the advancing freezing front during cryosurgery on living subjects. In the case of a catheter device placed into the urethra, the data may be further processed to yield a number, such as millimeters from the freezing front to the urethra, as will be shown. In this case, the output would be a number (a distance) rather than an image. This simplification would allow for a simple device that could warn the cryosurgeon when the advancing front is within a critical distance from the urethra. This is important, as freezing of such structures as the urethra or the colon are major causes of morbidity associated with these procedures.

Example 5
Classification for Detection of Nearby Objects

A simple proximity detector can be constructed from such a monitor. Proximity detection, such as the detection of nearby objects in turbid media, can be expensive and complicated. The present approach can be used to form an imaging probe located on the surface of skin, yet able to visualize the structure and character of the tissue below it. In this example, resin cylinder 556 containing a light-scattering Titanium dioxide suspension, similar in scattering properties to tissue, has embedded within it object 558, made of poorly absorbing solid Plexiglas™, which could represent a fluid-filled cyst (FIG. 10A). Using optical headband 352, as shown in FIG. 2E, cylinder 556 was imaged and object 558 is classified as fluid (diagonal lines), as shown in the resulting image of FIG. 10B. The output of a proximity detector need not be an image, an may be a number such as distance from the surface to the object 562 (FIG. 10C), or as a graph of percent fluid versus depth 564 (FIG. 10D). This numeric approach has the advantage of being easily interpreted, which may be useful, for example, in the detection of blood vessels under the surface of the skin.

This approach could be used as a noninvasive optical biopsy, characterizing tissue based upon optical properties to distinguish nerves, blood vessels, plaques on arteries, fat deposits, bleeding, air in tissues, bony growths, swelling, foreign objects, type of fluid in tissues or joints, normal tissue, or other inhomogeneities in tissue from one another.

Based upon the preceding examples, one could construct many types of diagnostic probes. For example, a needle fitted with classification fibers and hardware could warn if it is placed too close to a fragile structure, for example an aspiration needle placed near the spinal column to aspirate a herniated disk could warn if fragile nerve roots were about to be aspirated and damaged. Further, one could also use this approach to create a tool used to perform surgery, rather than merely monitoring the patient or performing a tissue diagnosis. For example, one can construct a surgical knife, studded with light emitting and detecting fibers. Such a knife would be able to optically image tissue directly under the knife while the knife is cutting, allowing the surgeon to visualize the tissue and structures about to be cut. If effect, this could allow the surgeon to avoid large blood vessels or nerves, or to better visualize the margins of a frozen tumor during cryosurgery. Last, a probe could be used to warn a physician that a structure has been picked up the forceps that might easily be unintentionally damaged, such as a ureter unintentionally grasped during fallopian tube surgery.

Example 6
Classification of Stroke as an Image

Figure 11:
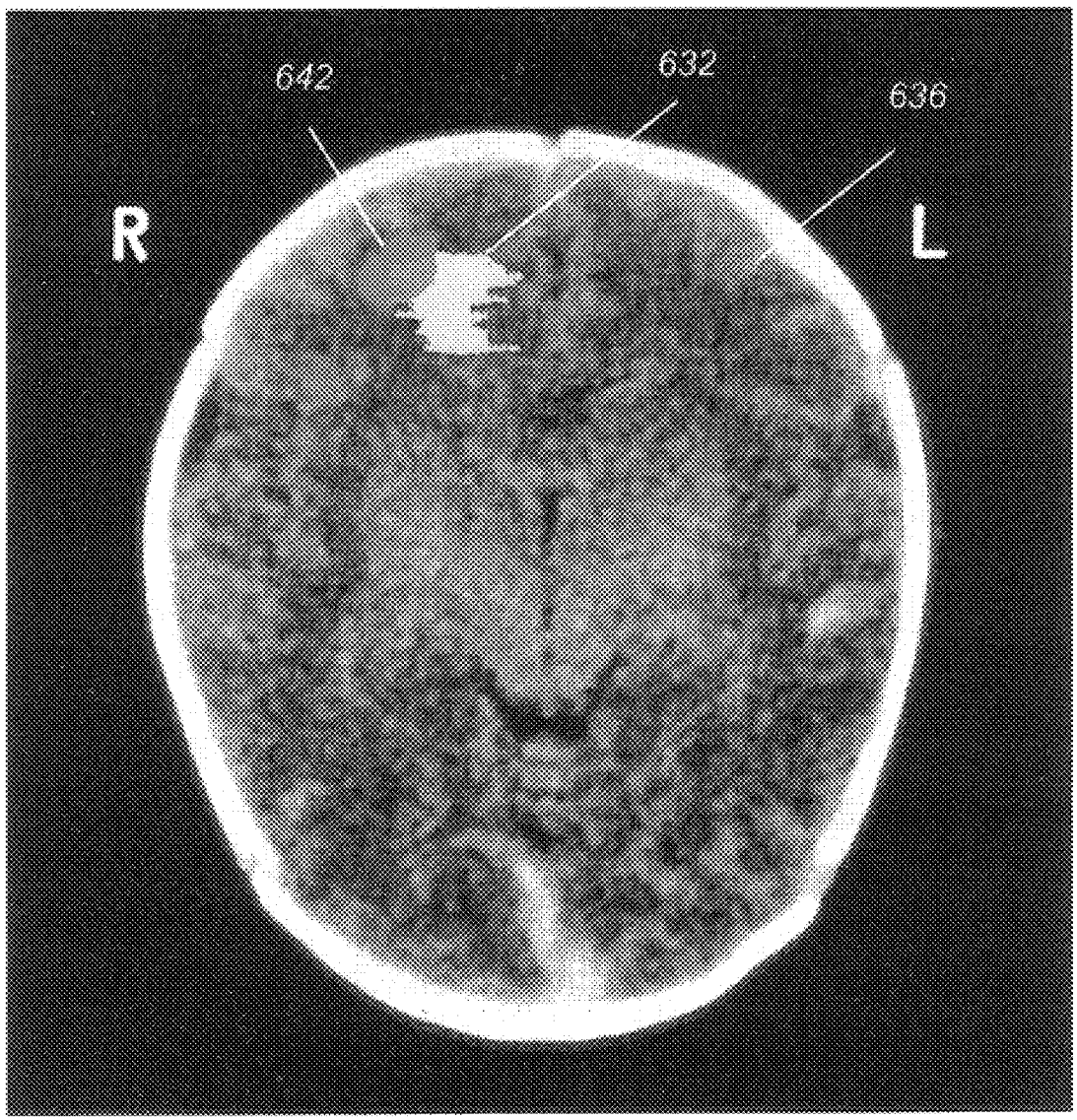
FIG. 11 is a photograph of a classified optical image of brain stroke.

The present approach can be combined with optical brain images to image oxygenation of brain or other tissue to allow classification of diseases such as stroke (FIG. 11).

In this example, optical scanning was performed using a soft, flexible fiber optic headband though which brief, low power (100 $\mu$W average, 60 ps FWHM) pulses of laser light are emitted and measured using time-resolved detection from multiple distributed locations. Pathologic changes in brain oxygenation were studied in ill infants with and without suspected hypoxic brain injury using optical imaging, with and without CT. For the stroke infant shown in FIG. 11, CT and optical imaging were sequentially performed, optical hemoglobin saturation was calculated, tomographically reconstructed, and an area of stroke 632 (yellow) was identified as the region having oxygenation more than 2 standard deviations below average. This image was overlaid on CT scan 636 (gray). Area of stroke 642 (red) on the CT scan was identified by a physician. There is overlap between optical and CT localization of stroke site, while optical scanning and classification alone was obtained at the bedside during a period of critical illness. Note also that optical stroke 632 was identified automatically using a classification analysis, while CT localization of the stroke 642 was performed manually by a physician.

In this example, the classification is for suspected stroke, but similar analysis allows imaging of tissue at risk for death or stroke in the future, based upon degree of blood flow, oxygenation, dye uptake, or other optical feature. The use of exogenous dyes can help such images. For example, a dye can be infused to mark the location of a stroke, as a lack of blood flow may show up as a delay in the dye reaching the area with low blood flow, or as a delay in clearance from this region of the brain. The ability to monitor and localize stroke noninvasively may allow for identification of existing or impending brain injury, providing opportunity for intervention.

Example 7
Classification of Brain Function as an Image

Figure 12:
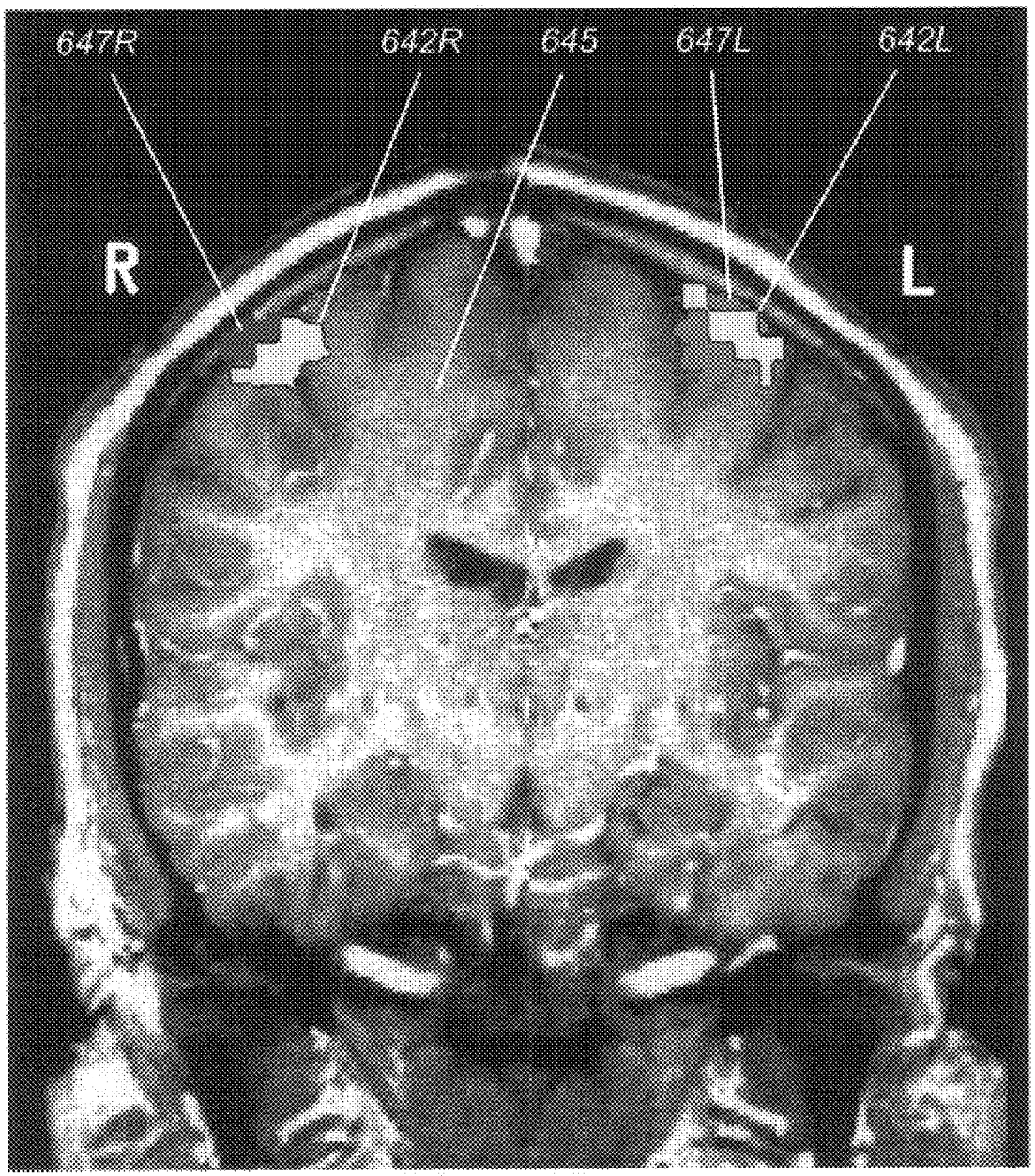
FIG. 12 is a photograph of a classified optical image showing brain functional activity.

In this example, the imaging of brain activation that occurs with movement of the hand is imaged (FIG. 12). As baseline brain oxygenation in nonactivated areas of the brain is stable over time, a resting state (baseline) can be subtracted from an activated state (motor task) to unmask a residual signal that is a function of local activation. Optical imaging was performed, with or without functional MRI during a sequential thumb-to-finger apposition task known to result in localized increases in brain blood volume and oxygenation. Increases in oxygenation during cortical activation were calculated from the optical data, tomographically reconstructed, and compared to functional MRI activation maps generated from the same subject. In this image, an area of the brain automatically identified as having an increase in oxygenation more than two standard deviations above baseline during right hand movement 642R and left hand movement 642L (yellow) are shown overlaid on a standard MRI scan 645 (gray). Localization of brain activity using functional MRI is shown during similar right hand movement 647R (blue) and left hand movement 647L (red). Using this approach, brain changes with hearing, thinking, and muscle movement can also be imaged.

Example 8
A Diagnostic Classifying Sensor for Uterine Disease

As a final example, a medical probe currently being introduced into clinical studies is now described. Abnormal (or dysfunctional) uterine bleeding is a very common problem in Gynecology. Unfortunately, it is difficult to diagnose, often ending in removal of the uterus (hysterectomy). One clue as to the need, or lack thereof, for hysterectomy is the presence of certain types of glandular tissue in the uterine wall, a condition called adenomyosis. This device is described under the preferred embodiment. In this device, the probe is invasive, and the changes in the detected optical spectrum are collected as the probe is advanced into the tissue, either manually or by automated mechanism. Alternatively, this data can be collected by noninvasive tomographic imaging, followed by classification. In the invasive approach, the distance into the tissue at which the glandular tissue is found is diagnostic of the disease of adenomyosis. The presence of glandular tissue beyond the glandular layer (myometrium) and into the muscular layer (myometrium) confirms the disease.

Figure 3B:
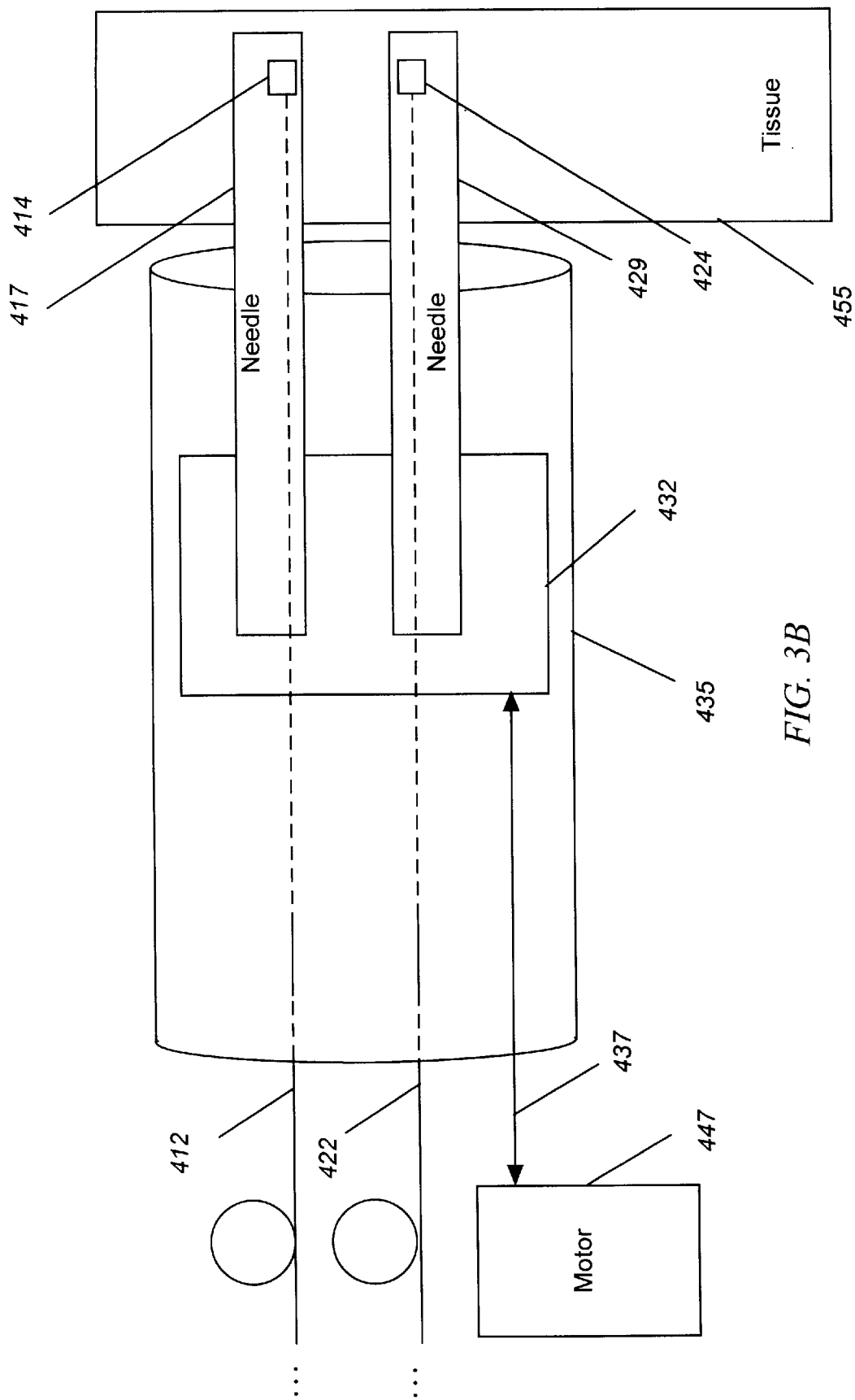

For these experiments, data is collected using the device in FIG. 1, and the moving needle probe shown in FIGS. 3A and 3B. The data is processed for percentage of glandular tissue as a function of depth, and displayed as a table for the clinician. For example, the following classification set could be considered normal, as the transition between a region that contains mostly glandular tissue to a region with minimal glandular tissue (in this case, between a region with a glandular content greater than 90% and a region with a glandular content of less than 10%, respectively) is sharp:

| Depth | % Glandular Tissue |
| --- | --- |
| 0 mm | 100% |
| 5 mm | 100% |
| 10 mm | 5% |
| 15 mm | 0% |
| 20 mm | 0% |

This tissue study would be interpreted as normal. Repetition of the test at different areas of the uterus would confirm that the majority of the uterus is free from deep glandular tissue sequestrations. One the other hand, the presence of glandular tissue deep in the muscular layer is indicated by the following, showing a large distance for transition between the glandular and muscular layers, which may be suspicious for adenomyosis:

| Depth: | % Glandular Tissue: |
| --- | --- |
| 0 mm | 100% |
| 5 mm | 100% |
| 10 mm | 75% |
| 15 mm | 40% |
| 20 mm | 40% |

In this second case, the presence of glandular tissue nearly 20 mm into the uterine wall is abnormal, and would likely be diagnosed by the obstetrician as adenomyosis. In fact, the glandular content is never less than 10% in this example. Repetition of this test at multiple sites would confirm the presence of either focal or diffuse adenomyosis. This diagnosis is made possible by the classification of tissue into, in this example, blood, muscular tissue, endometrium. The presence of a concentration of glandular tissue in the myometrium beyond a certain threshold level helps make the diagnosis.

Classification of the tissue types is performed by a computer, or by some calculating device specifically arranged to provide a classification function, and may be based upon stored reference spectra and diagnostic criteria (a reference library or database). In addition, the probe itself may contain some calibration and reference information that is transmitted to the diagnostic device during operation, allowing for the construction of smart probes programmed for identification of a specific tissue type or group of tissue types.

In addition to these examples, various additional modifications may be made within the spirit of this invention by those skilled in the art, and no undue limitation is to be implied of inferred from an omission of these items from the above description, and in the following disclosure. While the above disclosure has described one embodiment, it will apparent to those skilled in the art that various changes and modifications may be made therein, without departing from the spirit of the present invention. It is therefore stated that such changes and modifications all fall within the true spirit and scope of the present invention.

We have discovered an improved apparatus and method that measures tissue and allows the detection, quantification, localization, or characterization of one or more tissues within the observation field of the instrument. The device has been built and tested in several configurations, and has immediate application to several important problems, both medical and industrial, and thus constitutes an important advance in the art.

We claim:

1. A diagnostic monitor for classifying an unknown biological tissue into one or more tissue types, comprising:
   (a) a light emitter for illuminating the unknown tissue with at least one wavelength of illuminating radiation, said emitter optically coupled to the tissue;
   (b) a light detector for detecting an intensity of a portion of said illumination after having passed though a region of the tissue, and for providing a detected signal in response to said detected portion, said detector optically coupled to the tissue; and,
   (c) tissue classifier means for classifying the unknown tissue based upon said detected signal, wherein said classifier is operable to perform a computational comparison of said detected signal to a set of reference criteria in order to classify the unknown tissue, and for generating an output signal in response to said classification.

2. The monitor of claim 1, wherein the illuminating radiation has at least one wavelength between 200 nm and 100 μm.

3. The monitor of claim 1, wherein the emitter, the detector, or both the emitter and the detector, are arranged to be in physical contact with the tissue.

4. The monitor of claim 1, wherein the emitter, the detector, or both the emitter and the detector, are arranged to penetrate the tissue.

5. The monitor of claim 1, wherein the emitter is further comprised of multiple light emitting elements.

6. The monitor of claim 1, wherein the detector is further comprised of multiple light detecting elements.

7. The monitor of claim 1, wherein the classification means comprises means to classify the tissue by normal tissue type.

8. The monitor of claim 7, wherein said normal tissue type is selected from the group of types consisting of nerves, blood vessels, fat-deposits, and other normal tissue types.

9. The monitor of claim 1, wherein the classification means comprises means to characterize the tissue by abnormal tissue type.

10. The monitor of claim 9, wherein said abnormal tissue type is selected from the group of types consisting of hemorrhages, scars, cysts, tumors, and other pathologic tissue types.

11. The monitor of claim 1, wherein the classification means comprises means to localize the tissue.

12. The monitor of claim 11, wherein said localization comprises means to produce a measurement of distance.

13. The monitor of claim 11, wherein said localization comprises means to produce an image of the tissue.

14. The monitor of claim 1, wherein the classification means further comprises means for resolving multiple component tissue types contained within said tissue sample.

15. The monitor of claim 1, further including medical probe means for maintaining one or more of the emitter and detector elements in proximity to the sample tissue.

16. The monitor of claim 15, where the medical probe comprises a surgical tool.

17. An optical biopsy method for characterizing an unknown tissue sample, comprising the steps of:
   (a) illuminating the tissue sample with light of a number of discrete wavelengths;
   (b) detecting a measured intensity of a portion of said illumination after having propagated through a part of the tissue sample at said number of discrete wavelengths;
   (c) classifying the tissue sample based on a computational comparison of the measured intensity at one or more of said wavelengths to a set of reference criteria in order to classify the unknown tissue; and,
   (d) producing an optical biopsy output signal in response to the classification.

18. The method of claim 17, wherein the step of classification comprises the step of characterizing the tissue by normal tissue type selected from the group consisting of artery, vein, nerve, lymph, liver, muscle, brain, gray matter, white matter, colon, blood, or other normal tissue type.

19. The method of claim 17, wherein the step of classification comprises the step of characterizing the tissue by abnormal tissue type selected from the group consisting of hemorrhage, stroke, or other abnormal tissue type.

20. The method of claim 17, wherein the step of classification comprises the step of characterizing the tissue by component type selected from the group consisting of water, fat, hemoglobin, or other tissue component type.

21. The method of claim 17, wherein the step of classification comprises the step of localization of the tissue.

22. The method of claim 17, wherein the step of classification comprises the step of generating an image of the tissue.

23. The method of claim 17, wherein the step of classification further includes the step of resolving multiple component tissue types contained within the tissue sample.

24. The method of claim 17, wherein the step of classification further includes the step of comparing the detected signal to a reference signal.

25. The method of claim 17, wherein the step of classification further includes the step of comparing the detected signal to a set of reference database signals, said database composed of a library of characteristic signals from identified tissues.

26. The method of claim 17, further including the step of inducing a change in the tissue state, and wherein the step of classification comprises a classification of a change in the tissue.

27. The method of claim 26, wherein the step of inducing a change in the tissue comprises functional activation of the brain.

28. The method of claim 17 wherein said step of computational comparison includes the step evaluating the measured intensity relative to a predetermined threshold value.

29. The method of claim 17 wherein said step of computational comparison includes the step evaluating a ratio of the measured intensity at two discrete wavelengths relative to a predetermined threshold value.

30. The method of claim 17 wherein said step of computational comparison includes the step of evaluating changes in the measured intensity over space.

31. The method of claim 17 wherein said step of computational comparison includes the step of evaluating changes in the measured intensity over time.

32. The method of claim 17 wherein said step of computational comparison includes the step of evaluating, relative to a set of threshold values, a composition of the tissue, said composition selected from at least one of the group of measures consisting of blood content, blood oxygenation, air, fat, or other tissue components.

33. The method of claim 17 wherein said step of computational comparison includes the step of a evaluating a neural network, and wherein said reference criteria include threshold and operating values that characterize said network.

34. The method of claim 17 wherein said step of computational comparison includes the step of principal component analysis.

35. The method of claim 17 wherein said step of computational comparison includes the step of matrix analysis.

36. The method of claim 17, wherein the step of classifying includes the step of background subtraction.

37. The method of claim 17, wherein the step of classifying includes the step of measuring a reference illumination signal.

38. The method of claim 17, wherein the step of classifying includes the step of measuring a standard calibration reference.

39. The method of claim 17, wherein the step of classifying includes the step of correcting for instrument response.

40. The method of claim 17, wherein the step of classifying includes the steps of correcting the sample signal for light source, probe, and background characteristics to produce a final sample spectra.

41. A method of monitoring a regional change in state within a living tissue, said method comprising the steps of:
(a) illuminating said tissue with electromagnetic radiation in temporal proximity to a change in tissue state;
(b) detecting portions of said illuminating radiation have propagated through said tissue; and,
(c) characterizing, based upon said detected portions of illuminating radiation, at least one changing region of said tissue.

42. The method of claim 41, wherein said change in tissue state is a result of freezing the tissue.

43. The method of claim 41, wherein said change in tissue state is a result of heating the tissue.

44. The method of claim 41, wherein said change in tissue state is a result of thermally welding the tissue.

45. The method of claim 41, wherein said change in tissue state is a result of denaturing the tissue.

46. The method of claim 41, wherein said change in tissue state is a result of a function change in the tissue.

47. The method of claim 46, wherein said functional change is a measure of brain functional activity.

48. The method of claim 47, wherein said measure of brain activity is selected from the group consisting of hearing, thinking, sensory stimulation, muscle activation, sleep, or depth of anesthesia.

49. The method of claim 46, wherein said functional change is a measure of brain dysfunction.

50. The method of claim 49, wherein said measure of brain dysfunction is selected from the group consisting of stroke, seizure, and other types of brain dysfunction.

51. The method of claim 46, further comprising means for forming an image of said change in state.

52. An apparatus for detecting and classifying an unknown biological tissue in a medium that scatters a radiative wave, comprising:
(a) a radiative wave source arranged to emit radiation into the tissue;
(b) a radiative wave detector for detecting a portion of said radiation and providing a detected signal in response to said detected portion, said detected portion having passed through a region of said tissue; and,
(c) a computer for receiving said detected signal, said computer configured to classify the unknown tissue based upon a classification function of said detected signal, wherein said computer is operable to perform a comparison of said detected signal to a set of reference criteria in order to classify the unknown tissue, and for generating an output signal in response to said classification.

53. The spectrophotometer of claim 52, wherein said classification is a characterization of tissue by normal tissue type, said tissue type selected from the group consisting of nerves, blood vessels, fat deposits, and other normal macroscopic inhomogeneities in tissue.

54. The apparatus of claim 52, wherein said detector is comprised of a sensor configured to detect a radiative wave selected from the group of consisting of electromagnetic, electrical, pressure, sound, or other wave known to travel through biological material.

55. The apparatus of claim 54, wherein said detector is arranged to monitor both optical radiation and tissue pressure.

56. The apparatus of claim 52, wherein said detector is arranged to detect electrical waves as a function of tissue impedance.

57. The apparatus of claim 52, wherein said detector is comprised of more than one sensor, each configured to detect a radiative wave selected from the group of consisting of electromagnetic, electrical, pressure, sound, or other wave known to travel through biological material.

58. A method for noninvasively detecting at least one regional inhomogeneity in a turbid medium, comprising:
(a) illuminating said medium with electromagnetic radiation of at least one wavelength;
(b) detecting at least a portion of said illuminating radiation after said radiation has propagated through said medium over multiple non-parallel paths, and for providing output signals, said output signals being comprised of multiple regional component signals, said component signals detected after propagating through different regions of the medium;
(c) resolving said multiple regional component signals; and, (d) determining at least one quantifiable parameter influenced by said at least one regional inhomogeneity in the medium based upon at least one of said regional component signals.

59. A medical monitor for making measurement of tissue, comprising:
  (a) a light emitter for illuminating the tissue with at least one wavelength of illuminating radiation, said emitter optically coupled to the tissue;
  (b) a light detector for detecting an intensity of a portion of said illuminating radiation after having passed though the tissue, and for providing a detected signal in response to said detected portion, said detector optically coupled to the tissue; and,
  (c) tissue classifier means for receiving said detected signal, for determining the presence or absence of at least one target tissue based upon said comparison, and for generating an output signal in response to said determination, wherein said classifier is operable to perform a computational comparison of said detected signal to a database of stored reference spectra and diagnostic criteria in order to classify the unknown tissue.

60. The monitor of claim 59, wherein said tissue is the uterus, and said target tissue is adenomyosis.

61. The monitor of claim 59, wherein said tissue is brain, and said target tissue is cerebral stroke.

62. The monitor of claim 59, wherein said tissue is the spine, and said target tissue is nerve.

63. The monitor of claim 59, wherein said tissue is the prostate, and said target tissue is prostate cancer.

64. The monitor of claim 59, wherein said determination is a probabilistic calculation of the likelihood of presence or absence of the target tissue.

65. The monitor of claim 59, wherein said tissue is a portion of the human body, said target tissue is cancer.

66. The monitor of claim 59 wherein said reference criteria include one or more criteria selected from the group consisting of hemoglobin content, blood oxygenation, and optical scattering.

* * * * *